United States Patent [19]

Naora et al.

[11] Patent Number: 4,849,535
[45] Date of Patent: * Jul. 18, 1989

[54] PRODUCTION OF CYCLOPENTENYLHEPTANOIC ACID DERIVATIVES

[75] Inventors: Hirokazu Naora, Kawasaki; Takashi Onuki, Yokohama; Asao Nakamura, Tokyo, all of Japan

[73] Assignees: Ajinomoto Co., Inc.; Mochida Pharmaceutical Co., Ltd., both of Tokyo, Japan

[*] Notice: The portion of the term of this patent subsequent to Apr. 14, 2004 has been disclaimed.

[21] Appl. No.: 831,852

[22] Filed: Feb. 24, 1986

[30] Foreign Application Priority Data

Feb. 26, 1985 [JP] Japan ................................ 60-37167

[51] Int. Cl.$^4$ ........................................... C07C 177/00
[52] U.S. Cl. .................... 556/441; 560/121; 562/503
[58] Field of Search ................. 560/121; 562/503; 556/441

[56] References Cited

U.S. PATENT DOCUMENTS 3,922,299 11/1975 Heck ..................................... 560/76
4,658,055 4/1987 Onuki ................................... 562/503

OTHER PUBLICATIONS

Heck, Accts of Chem. Res. 12 147 (1979).
Novak, Chem. Ber., 113, 2939 (1980).

Primary Examiner—Robert Gerstl
Attorney, Agent, or Firm—Oblon, Spivak, McClelland, Maier & Neustadt

[57] ABSTRACT

Cyclopentenylheptanoic acid derivatives having the formula:

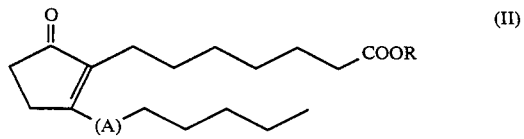

wherein R is hydrogen or $C_1$ to $C_4$ alkyl and —(A)— is:

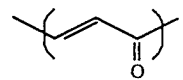

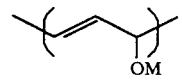

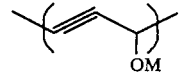

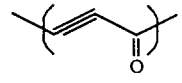

wherein M is hydrogen or triorganosilyl group, are prepared by reacting a compound having the formula:

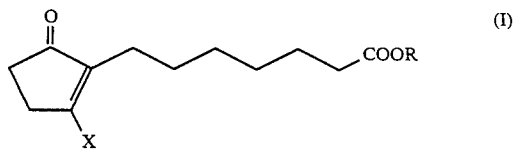

ps wherein X is halogen, with a compound having the formula:

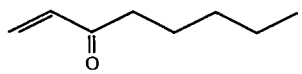

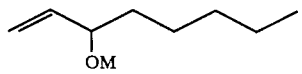

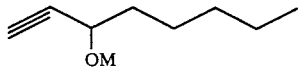

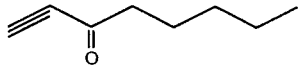

The derivatives belong to the pharmacologically-active class of compounds called "prostaglandins".

7 Claims, No Drawings

PRODUCTION OF CYCLOPENTENYLHEPTANOIC ACID DERIVATIVES

BACKGROUND OF THE INVENTION

1. Field of the invention

This invention relates to a novel method for the production of cyclopentenyl heptanoic acid derivatives, which derivatives belong to the class of compounds called "prostaglandins".

Prostaglandins possess many pharmacological effects such as the ability to impede the coagulation of blood platelets, the ability to lower or elevate blood pressure, the ability to contract smooth muscles, and the ability to suppress the excretion of gastric juices. Prostaglandins therefore are useful as drugs for the prevention and cure of various diseases such as thrombosis, hypertension and peptic ulcers.

2. Description of the prior art

There are many known methods for the production of prostaglandins. All of these known methods are long and complicated (see, for example, Agr. and Biol. Chem., 33, 1078 (1969); J. Amer. Chem. Soc., 91, 5675 (1969); J. Amer. Chem. Soc., 92, 2586 (1970); Chem. Pharm. Bull., 17 408, 1969.). For example, in order to synthesize prostaglandin $B_1$, at least 10 steps are needed, starting from malonic acid diethyl ester. Therefore, this known method is not advantageous industrially, in view of the yield and the complexity. Accordingly, there exists a need for the development of a commercially advantageous method for the production of prostaglandins.

SUMMARY OF THE INVENTION

The inventors of the present invention have studied earnestly to develop a method for the production of prostaglandins easily and at a low cost, and found that reaction of a compound having the general formula:

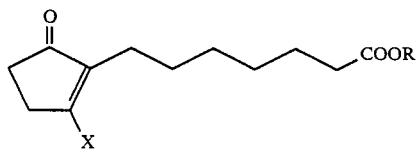
(I)

with any one of the compounds having the following structures:

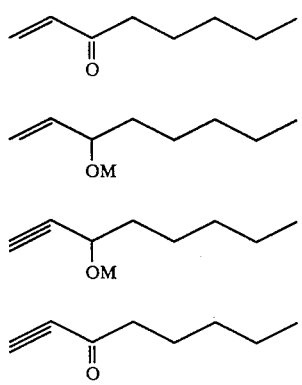

produces a cyclopentenyl heptanoic acid derivative having the formula:

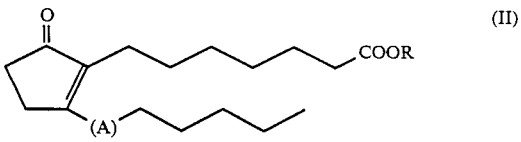
(II)

and have completed the present invention on the basis of such findings. In the above general formulae, R is a hydrogen atom or an alkyl group having from 1 to 4 carbon atoms, X is a halogen atom such as a chlorine atom, a bromine atom or an iodine atom, M is a hydrogen atom or a triorganosilyl group, and -(A)- is any one of the groups having the formulae:

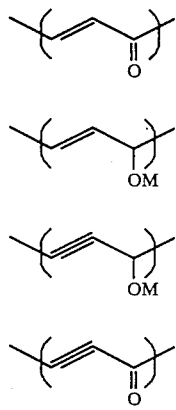

In the above reaction, a solvent is preferably employed, and the reaction is preferably carried out in the presence of a palladium salt such as palladium acetate, an organophosphorus compound such as triphenylphosphine or an amine such as triethylamine. A solvent is not necessarily needed; however, its use makes the operation of the reaction easier. Examples of the solvent are acetonitrile, N,N'-dimethyl formamide (DMF) and alcohols.

The compound (I) used as the starting material in the present invention can be easily produced by reacting a heptanoic acid derivative having the formula:

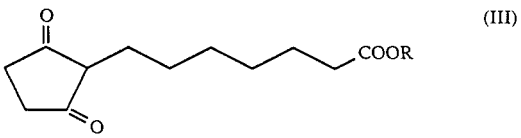
(III)

wherein R has the same meaning as above, with a halogen such as chlorine, bromine or iodine. In such a case, a solvent is preferably employed and the reaction is preferably carried out in the presence of an organophosphorus compound such as triphenyl phosphine. A phosphorus halide such as phosphorus trichloride or phosphorus tribromide can be used instead of the foregoing reagent. As the solvent, a solvent of aprotic nature, such as benzene, toluene, DMF, benzonitrile or acetonitrile, is preferably employed.

The compound (III) wherein R is a hydrogen atom may be obtained by the treatment of the reaction mixture with water.

The compound (III) wherein R is an alkyl group may be obtained by treating the reaction mixture with an alcohol, and then treating the product thus obtained with water to effect a decomposition. For example, the reaction mixture is treated with methyl alcohol and the product thus treated is decomposed with water to produce a methyl ester derivative.

The compound (I) wherein X is a bromine atom may be treated with sodium iodide in a solvent, for example acetone, methyl ethyl ketone or DMF, to provide the compound (I) wherein X is an iodine atom. The compound (I) wherein X is a bromine or iodine atom is novel, and is an important intermediate for the production of prostaglandins.

As regards the starting materials for use in the present invention, it has been already found by the present inventors (see EP-A No. 0150996) that 7-(2,5-dioxocyclopentyl) heptanoic acid of high purity is produced very easily and inexpensively by subjecting 1-cyclooctenyl acetate, 1-cyclooctenyl oxytriorganosilane or 1-alkoxycyclooctene (and related compounds), and succinic anhydride or succinyl halide to a Friedel-Crafts reaction and treating the resulting reaction product with water, an aqueous acid or an alkaline solution.

Specifically, a heptanoic acid derivative having the formula:

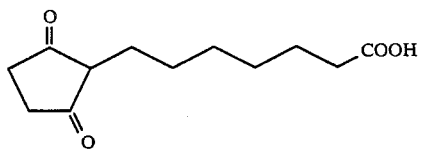

is produced by the reaction of a cyclooctene derivative having the formula:

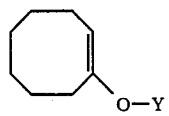

wherein Y is $-R^1$, $-COR^1$ or $-SiR^2_3$ with a compound having the formula:

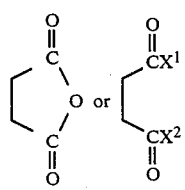

In the foregoing formulae, $R^1$ is an alkyl group having from 1 to 5 carbon atons, an aryl group or an aralkyl group, $R^2$ is an alkyl group having from 1 to 5 carbon atoms, an aryl group such as phenyl group, or an aralkyl group such as benzyl group, and $X^1$ and $X^2$ are each a halogen atom such as chlorine or bromine, with $X^1$ and $X^2$ preferably being same.

As the catalyst, a Lewis acid for use in Friedel-Crafts reactions is adopted. Examples of the Lewis acid are aluminum chloride, aluminum bromide, tin chloride, boron trifluoride, zinc chloride and titanium tetrachloride.

It is not necessary to use a solvent for the reaction; however, when a solvent is used, it helps to promote the reaction. Examples of the solvent are methylene chloride, 1,2-dichloroethane, nitromethane, nitrobenzene, 1,1,2-trichloroethane and 1,1,2,2-tetrachloroethane.

The presence of a halotrialkylsilane (having, for example, about 1 to 5 carbon atoms in the alkyl group thereof) such as chlorotrimethylsilane in the reaction system proves advantageous because these compounds improve the yields.

It has been found that the isolation of 7-(2,5-dioxocyclopentyl) heptanoic acid from the reaction mixture and the refinement of the separated acid can be accomplished in a simple manner, for example by extraction with a solvent, extraction with an aqueous alkaline solution and washing with water. Accordingly, the above mentioned method may be said to be extremely easy and advantageous.

In this invention, when 1-cyclooctenyl acetate is selected as the cyclooctene derivative for use as the starting material, the acetate derivative of the desired product can be produced very easily in high yield by the reaction of isopropenyl acetate with cyclooctanone in the presence of an acid. When 1-cyclooctenyl oxytrimethylsilane is selected as the starting material, the cyclooctene derivative of the desired product can be prepared by the reaction of chlorotrimethylsilane with cyclooctanone in the presence of triethylamine. When 1-alkoxycyclooctene is selected as the starting material, the cyclooctene derivative of the desired product can be produced by the reaction of an alkyl orthoformate with cyclooctanone in the presence of an acid.

Those specific reactions are examples of those that can be carried out, using various starting materials, and many variations thereof will readily produce the same results as will be appreciated by those skilled in the art.

By the present invention, via the 7-(2,5-dioxocyclopentyl) heptanoic acid derivatives, prostaglandins can be produced very easily and inexpensively as described above, and accordingly the present invention is very useful. In this respect, the known method for the production of prostaglandin $B_1$, using malonic acid diethyl ester as a starting material, is as follows:

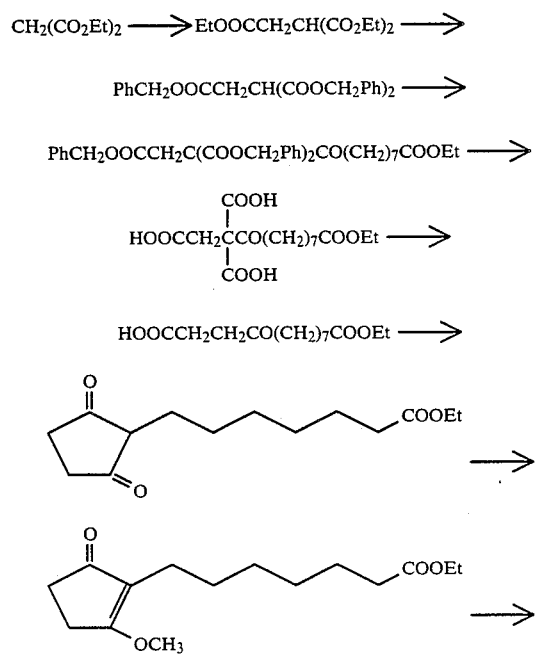

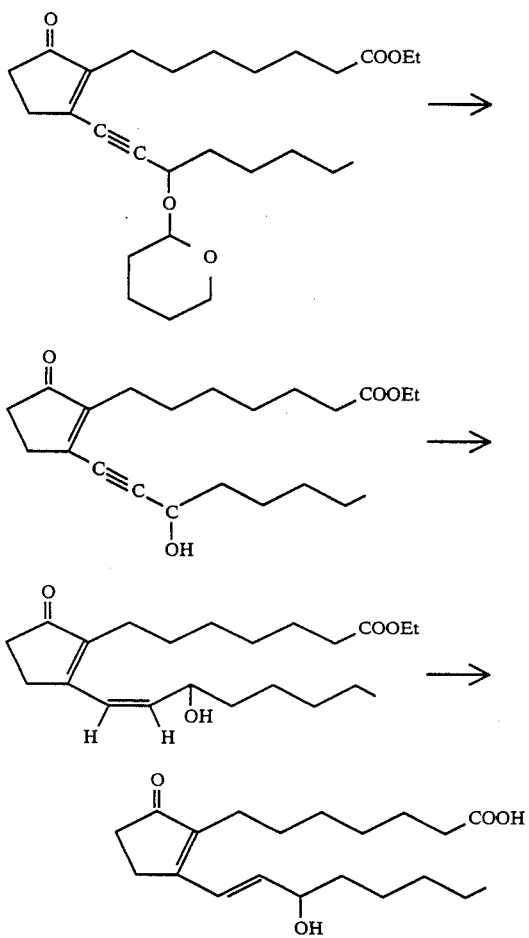

As described before, the present invention permits the prostaglandins to be produced from cyclooctanone as the starting material through only 4 steps. The procedure of the reaction and isolation and the purification of the product are extremely simple. Thus, the present invention is decisively improved over the conventional method in terms of production process, equipment and the like.

The invention now being generally described, the same will be better understood by reference to the following examples which are included for purpose of illustration only and are not to be considered limiting of the invention unless otherwise specified.

EXAMPLES

Example 1

15-dehydro-prostaglandin $B_1$ methyl ester (9,15-dioxoprosta-8,13-dienoic acid methyl ester)

Production of 7-(2,5-dioxocyclopentyl) heptanoic acid

The title compound was produced in any one of the following processes A to N.

(A) In the presence of 0.6 g of paratoluenesulfonic acid, 50 g (0.4 mol) of cyclooctanone and 100 ml (0.9 mol) of isopropenyl acetate were refluxed for 11 hours. The reaction mixture was cooled, stirred with 0.6 g of anhydrous sodium carbonate at room temperature for one hour, left standing overnight, and filtered. The filtrate was distilled under reduced pressure to afford 60 g (91% yield) of 1-cyclooctenyl acetate having a boiling point of 71° to 73° C./3 mmHg.

In 5 ml of 1,2-dichloroethane, 2.7 g of aluminum chloride was suspended. To the resultant suspension, 1 g (10 mmol) of succinic anhydride was added and then 1.66 g (10 mmol) of 1-cyclooctenyl acetate obtained as described above was added dropwise over a period of about three minutes. The resultant mixture was stirred at room temperature for one hour. This mixture was stirred at 70° C. for five hours, then cooled, poured into 50 ml of 1N hydrochloric acid containing ice, and extracted three times with 30 ml of ethyl acetate. The extract was concentrated, and the residue was stirred with 30 ml of a saturated aqueous sodium bicarbonate solution and 30 ml of ether and separated. The residue was again stirred with 20 ml of a saturated aqueous sodium bicarbonate solution and 20 ml of ether, and separated. The aqueous layers were combined and washed three times with 20 ml of ether. The aqueous layer was adjusted to pH 1–2 with 6N hydrochloric acid and extracted with ethyl acetate. The organic layer was dried and concentrated. The residue was washed twice with 3 ml of water and dried. Consequently, 0.24 g (11% yield) of 7-(2,5-dioxocyclopentyl) heptanoic acid was obtained. This product had a melting point of 138° to 146° C. The IR and NMR spectra of this product agreed with those of a sample produced by a previously known method of synthesis.

(B) In 5 ml of 1,2-dichloroethane, 2.7 g of aluminum chloride was suspended. To the resultant suspension, 1.6 g (10 mmols) of succinyl chloride and 1.7 g (10 mmols) of 1-cyclooctenyl acetate were added at room temperature. The resultant mixture was stirred at 70° C. for five hours. The resultant mixture was poured into 50 ml of 1N hydrochloric acid containing ice and extracted three times with 30 ml of ethyl acetate. The aqueous layer that was extracted from the ethyl acetate layer twice with 30 ml of a saturated aqueous sodium bicarbonate solution was washed with ethyl acetate, adjusted to pH 1 to 2, and again extracted three times with 30 ml of ethyl acetate. The organic layer was dried and concentrated. The residue was washed with water to give 0.2 g (9% yield) of 7-(2,5-dioxocyclopentyl) heptanoic acid. It had a melting point of 135° to 146° C.

(C) To a suspension of 2.5 g of aluminum chloride in 10 ml of 1,2-dichloroethane, 1 g of succinic anhydride was added. The reaction mixture was stirred at room temperature for one and a half hours. To the mixture, 1.7 g of 1-cyclooctenyl acetate was added under cooling with ice over a period of three minutes. The resultant mixture was stirred at room temperature for 10 minutes. Then the mixture was refluxed for four hours, cooled, and poured into 50 ml of 1N hydrochloric acid containing ice. The reaction mixture was extracted four times with 30 ml of ethyl acetate. The organic layer was extracted with 30 ml of a saturated aqueous sodium bicarbonate solution. The extract was washed three times with 20 ml of ethyl acetate at pH 7. The aqueous layer was adjusted to pH 2 with 6N hydrochloric acid and extracted four times with 30 ml of ethyl acetate. The extract was dried and concentrated. The residue was washed with water to give 0.2 g of 7-(2,5-dioxocyclopentyl) heptanoic acid having a melting point of 110° to 125° C. The IR and NMR spectra of this compound agreed with those of an authentic sample.

(D) To a solution of 2.7 g of aluminum chloride in 15 ml of nitromethane, 1.0 g of succinic anhydride was added, and then 1.7 g of 1-cyclooctenyl acetate was added dropwise under cooling. The resultant mixture was stirred at room temperature overnight and refluxed with stirring for four hours. The mixture was cooled, poured into 50 ml of 1N hydrochloric acid containing ice, and extracted four times with 30 ml of ethyl acetate. The organic layer was extracted twice with 30 ml of a saturated aqueous sodium bicarbonate solution. The aqueous layer was washed with ethyl acetate at pH 7. The aqueous was adjusted to pH 2 with 6N hydrochloric acid, and again extracted four times with 30 ml of ethyl acetate. The extract was dried and concentrated. The residue was washed with water to give 0.2 g of 7-(2,5-dioxocyclopentyl) heptanoic acid. This product had a melting point of 105° to 122° C.

(E) To a solution of 42 g (0.38 mol) of chlorotrimethylsilane and 78 g of triethylamine in 100 ml of dimethylformamide, a solution of 32 g (0.254 mol) of cyclooctanone in 40 ml of dimethylformamide was added. The resultant mixture was stirred at 100° to 115° C. for 48 hours. At the end of the reaction, the reaction mixture was combined with 240 ml of n-hexane and washed twice with 300 ml of a saturated aqueous sodium bicarbonate solution. The mixture was washed under cooling with 180 ml of 1.5N hydrochloric acid, then washed sequentially with an aqueous sodium bicarbonate solution, water, and saline and then dried with magnesium sulfate. The mixture was concentrated and distilled under vacuum, to afford 40 g (80% yield) of 1-cyclooctenyloxytrimethylsilane having a boiling point of 82° to 84° C./5 mmHg.

To a suspension of 2.6 g of aluminum chloride in 7 ml of 1,2-dichloroethane, 1 g (10 mmol) of succinic anhydride was added and stirred at room temperature for one hour. To the resultant mixture, 2 g (10 mmol) of 1-cyclooctenyloxytrimethylsilane obtained as described above was added over a period of three minutes. The reaction mixture was stirred at room temperature for one hour and heated for 24 hours at 80° C. The resultant reaction mixture was cooled, poured into 50 ml of 1N hydrochloric acid containing ice, and extracted five times with 30 ml of ethyl acetate. The organic layer was extracted with 40 ml of a saturated aqueous sodium bicarbonate solution. The mixture was washed once with 20 ml of ethyl acetate at pH 7. The aqueous layer was adjusted to pH 1.5 with 6N hydrochloric acid and extracted three times with 30 ml of ethyl acetate. The extract was concentrated and the residue was washed with 3 ml of water. Consequently, 0.2 g (9% yield of 7-(2,5-dioxocyclopentyl) heptanoic acid having a melting point of 131° to 141° C. was obtained.

The IR and NMR spectra of this compound agreed with those of an authentic sample.

(F) To a suspension of 2.6 g (20 mmol) of aluminum chloride in 15 ml of 1,2-dichloroethane, 1 g (10 mmol) of succinic anhydride was added. The reaction mixture was stirred at room temperature for one hour. To the resultant mixture, 1.7 g (10 mmol) of 1-cyclooctenyl acetate was added under cooling with ice. The reaction mixture was stirred at room temperature for 10 minutes and then heated at 80° C. for 28 hours. The reaction mixture was cooled and poured into 50 ml of 1.5N hydrochloric acid containing ice. The reaction mixture was extracted four times with 30 ml of ethyl acetate. The organic layer was extracted with 40 ml of a saturated aqueous sodium bicarbonate solution. The aqueous layer was adjusted to pH 1.5 with 6N hydrochloric acid and extracted four times with 30 ml of ethyl acetate. The organic layer was washed with 30 ml of saline. The resultant mixture was concentrated. The residue was washed with 5 ml of water to give 0.40 g (18% yield) of 7-(2,5-dioxocyclopentyl) heptanoic acid having a melting point of 133° to 138° C. The IR and NMR spectra of this compound agreed with those of an authentic sample.

(G) To a suspension of 2.6 g of aluminum chloride in 10 ml of 1,2-dichloroethane, 1 g of succinic anhydride was added. The reaction mixture was stirred at room temperature for 1.5 hours. To the resultant mixture, 1.7 g of 1-cyclooctenyl acetate and 2.5 g of chlorotrimethylsilane were added in the order mentioned under cooling with ice. The resultant mixture was stirred at room temperature for 20 hours and heated at 80° C. for 28 hours. The reaction mixture was cooled and poured into 50 ml of 1.5N hydrochloric acid containing ice. The mixture was extracted four times with 30 ml of ethyl acetate. The organic layer was extracted with 50 ml of a saturated aqueous sodium bicarbonate solution and 30 ml of water sequentially in the order mentioned. The aqueous layer was adjusted to pH 1.5 with 6N hydrochloric acid and extracted four times with 30 ml of ethyl acetate. The organic layer was washed with 30 ml of saline and concentrated. The residue was washed with 5 ml of water. Consequently, 0.53 g (24% yield) of 7-(2,5-dioxocyclopentyl) heptanoic acid having a melting point of 131° to 138° C. was obtained.

(H) To a suspension of 5.5 g of aluminum bromide in 10 ml of 1,2-dichloroethane, 1.1 g of succinic anhydride was added. The reaction mixture was stirred at room temperature for one hour. To the resultant mixture, 1.9 g of 1-cyclooctenyl acetate was added under cooling with ice. The resultant mixture was stirred at room temperature for 30 minutes and heated at 80° C. for 27 hours. The reaction mixture was cooled, poured into 1.5N hydrochloric acid containing ice, and extracted five times with 40 ml of ethyl acetate. The organic layer was extracted with 50 ml of a saturated aqueous sodium bicarbonate solution and 20 ml of water. The aqueous solution was adjusted to pH 1.5 and extracted four times with 40 ml of ethyl acetate. The organic layer was washed with 30 ml of saline and concentrated. The residue was washed with 5 ml of water to yield 0.44 g of 7-(2,5-dioxocyclopentyl) heptanoic acid having a melting point of 129° C. to 137° C. The IR and NMR spectra of this compound agreed with those of an authentic sample.

(I) To a solution of 4 g of titanium tetrachloride in 5 ml of 1,2-dichloroethane, 1.08 g of succinic anhydride was added at room temperature. The resultant mixture was stirred for 30 minutes. To the resultant mixture, 1.79 g of 1-cyclooctenyl acetate was added. The mixture was stirred at room temperature for 30 minutes, refluxed for 45 hours, cooled, and poured into 50 ml of 1N hydrochloric acid containing ice. The resultant mixture was extracted three times with 30 ml of ethyl acetate. The ethyl acetate layer was washed with water and saline. The organic layer was extracted twice with 30 ml of a saturated aqueous sodium bicarbonate solution. The aqueous layers were combined and washed twice with 30 ml of ethyl acetate, at pH 7.05. The aqueous layer was adjusted to pH 1.5 and extracted five times with 30 ml of ethyl acetate. The extract was dried and concentrated to afford 262.7 mg of a solid. The solid was washed twice with 1 ml of water. Consequently, 0.04 g of 7-(2,5-dioxocyclopentyl) heptanoic acid having a melting point of 135° to 143° C. was obtained.

(J) To a suspension of 2.6 g of aluminum chloride in 7 ml of 1,1,2-trichloroethane, 1 g of succinic anhydride was added. The mixture was stirred at room temperature for one hour. To the resultant mixture, 1.7 g of 1-cyclooctenyl acetate was added at room temperature. The reaction mixture was stirred for one hour and refluxed for 24 hours. The reaction mixture was cooled, poured into 50 ml of 1.5N hydrochloric acid containing ice, and extracted five times with 40 ml of ethyl acetate. The organic layer was washed once with 30 ml of water and extracted with 30 ml of a saturated aqueous sodium bicarbonate solution and 20 ml of water. The aqueous alkaline layer was adjusted to pH 1.5 and extracted four times with 40 ml of ethyl acetate. The organic layer was washed with 30 ml of saline and concentrated. The residue was washed with 6 ml of water to give 0.36 g of 7-(2,5-dioxocyclopentyl)heptanoic acid having a melting point of 124° to 134° C. The IR and NMR spectra of this compound agreed with those of an authentic sample.

(K) To a suspension of 2.6 g of aluminum chloride in 6 ml of 1,1,2,2-tetrachloroethane, 1 g of succinic anhydride was added. The reaction mixture was stirred at room temperature for one hour. To the resultant mixture, 1.7 g of 1-cyclooctenyl acetate was added at room temperature. The mixture was stirred for 1.5 hours and then refluxed for 22 hours. The reaction mixture was cooled, poured into 50 ml of 1.5N hyrochloric acid containing ice, and extracted five times with 40 ml of ethyl acetate. The organic layer was washed once with 30 ml of water, and extracted with 40 ml of a saturated aqueous sodium bicarbonate solution and 20 ml of water. The aqueous extract was adjusted to pH 1 and extracted four times with 40 ml of ethyl acetate. The organic layer was washed with 30 ml of saline and concentrated. The residue was washed with 3 ml of water to give 0.27 g of 7-(2,5-dioxocyclopentyl) heptanoic acid having a melting point of 127° to 135° C.

(L) To a suspension of 2.66 g of aluminum chloride in 1.55 g of succinic chloride, 1.66 g of 1-cyclooctenyl acetate was added at 0° C. The resultant mixture was stirred at room temperature for 20 minutes and then at 80° C. for 18 hours. The resultant mixture was poured into 50 ml of 1N hydrochloric acid containing ice and extracted three times with 30 ml of ethyl acetate. The ethyl acetate layer was washed with water and saline, and then extracted three times with 30 ml of a saturated aqueous sodium bicarbonate solution. The aqueous extract was washed with ethyl acetate, adjusted to pH 1-2, and extracted six times with 30 ml of ethyl acetate. The extract was dried and concentrated, to afford 263.9 mg of a solid. The solid was washed twice with 1 ml of water. Consequently, 0.15 g (7% yield) of 7-(2,5-dioxocyclopentyl) heptanoic acid having a melting point of 130° to 140° C. was obtained. The IR and NMR spectra of this compound agreed with those of an authentic sample.

(M) In the presence of 0.2 g of paratoluenesulfonic acid, 16.5 g (0.13 mol) of cyclooctanone and 16.5 g (0.15 mol) of trimetyl orthoformate were stirred at room temperature for four hours. The resultant mixture was heated at 100° C. for 14 hours. The vacuum distillation of the mixture gave 13.7 g (75% yield) of 1-methoxycyclooctene having a boiling point of 83° to 88° C./27 mmHg.

To a suspension of 2.6 g of aluminum chloride in 6 ml of 1,2-dichloroethane, 1 g (10 mmol) of succinic anhydride was added. The resultant mixture was stirred at room temperature for one and a half hours. To the resultant mixture, 1.5 g (11 mmol) of 1-methoxycyclooctene obtained as described above was added with stirring. The mixture was heated at 85° C. for 63 hours. The reaction mixture was cooled, poured into 50 ml of ice water, and extracted twice with 50 ml of butanol. The butanol layer was washed three times with 30 ml of water, combined with 20 ml of water, and adjusted to pH 6.9 with stirring. The aqueous layer was washed twice with 20 ml of butanol and adjusted to pH 2.0. The aqueous layer was extracted twice with 30 ml of butanol. The butanol layer was washed twice with 20 ml of water and concentrated to afford 0.6 g of a solid. The solid was washed with 3 ml of water, to afford 0.38 g (17% yield) of 7-(2,5-dioxocyclopentenyl) heptanoic acid having a melting point of 145° to 151° C. The NMR spectrum of this compound agreed with that of an authentic sample.

(N) In the presence of 0.3 g of paratoluenesulfonic acid, 20 g (0.16 mol) of cyclooctanone and 27 g (0.18 mol) of ethyl orthoformate were stirred at room temperature overnight. The resultant mixture was heated at 100° C. for 15 hours and distilled under reduced pressure to give 10.9 g (45% yield) of 1-ethoxycyclooctene having a boiling point of 97.5° to 98.5° C./25 mmHg.

NMR (deuterated chloroform) spectrum.

| δ: | | |
|---|---|---|
| | 4.39 (t, J = 8Hz, 1H) | olefinic-hydrogen |
| | 3.60 (quartet, J = 7Hz, 2H) | O—$CH_2CH_3$ |
| | 2.35 − 1.70 (m, 4H) | $CH_2$—at allyl position |
| | 1.60 − 1.30 (m, 8H) | $CH_2$—× 4 |
| | 1.25 (t, J = 7Hz, 3H) | O—$CH_2CH_3$ |

To a suspension of 2.6 g of aluminum chloride in 10 ml of 1,2-dichloroethane, 1 g (10 mmol) of succinic anhydride was added. The mixture was stirred at room temperature for two hours. To the resultant mixture, 1.7 g (11 mmol) of 1-ethoxycyclooctene obtained as described above was added with cooling. The resultant mixture was stirred at room temperature for 10 minutes and heated at 85° C. for 69 hours. The reaction mixture was cooled, poured into 50 ml of ice water, and extracted twice with 50 ml of butanol. The organic layer was washed three times with 30 ml of water. The organic layer was combined with 20 ml of water and adjusted to pH 6.9 with 1N NaOH with stirring. The aqueous layer was washed twice with 20 ml of butanol and adjusted to pH 2.0. The aqueous layer was extracted twice with 30 ml of butanol. The butanol extract was washed twice with 20 ml of water and concentrated. Consequently, 0.39 g of a solid was obtained. This solid was washed with 2 ml of water, to afford 220 mg (10% yield) of 7-(2,5-dioxocyclopentyl) heptanoic acid having a melting point of 143° to 148° C. The NMR and IR spectrum and TLC Rf value agreed with those of an authentic sample.

Production of 7-(2-bromo-5-oxo-1-cyclopentyl) heptanoic acid methyl ester

The title substance was produced by either one of the following process (A) and (B).

(A) Dried triphenyl phosphine (5.76 g) was dissolved in dried benzene (150 ml), and then 1M bromine in benzene solution (22 ml) was added thereto while stirring at 0° C. over 3 minutes. The mixture was stirred for 10 minutes at room temperature, and then dried triethyl amine (3 ml) was added thereto at 0° C. Continuously, 7-(2,5-oxocyclopentyl) heptanoic acid (2.26 g) was added thereto. The mixture thus obtained was stirred for 24 hours at room temperature, and dried methanol (2 ml) was added thereto. It was stirred for 2 minutes and the reaction mixture was poured into the same volume of water, and the solution was extracted with three 200 ml portions of ether. The ether layer thus extracted was washed with water and a saturated aqueous sodium chloride solution, and dried over anhydrous magnesium sulfate. The solvent was distilled off therefrom and the resultant residue was purified by silica gel column chromatography (solvent: a mixture of hexane and ethyl acetate) to afford the object product (yield 1.86 g, 61.4%).

Mass Spectrum (MS) m/z: 304, 302, 273, 271, 223, 191.

IR Spectrum (Liquid Film Method) cm$^{-1}$: 1735, 1705, 1625.

NMR Spectrum (CDCl$_3$; Internal standard: TMS) δ: 1.2–1.8 (m, 8H); methylene group in 3 to 6 positions, 2.1–2.4 (m, 4H), 2.4–2.6 (m, 2H) and 2.8–3.0 (m, 2H); methylene group in 2, 7, 10 and 11 positions, 3.6 (s, 3H); —COoMe.

(B) 7-(2,5-Dioxocyclopentyl) heptanoic acid (0.55 g) was suspended in chloroform (8 ml) and phosphorus tribromide (1.03 g) dissolved in chloroform (2 ml) was added thereto over 2 minutes at room temperature. The mixture was refluxed by heating for 5 hours and cooled, and then dried methanol (1 ml) was added thereto under cooling with ice. The mixture was stirred for 30 seconds and then poured into ice-water (30 ml). The solution was extracted with three 35 ml portions of ether and the extract solution was washed with two 20 ml portions of water, a saturated aqueous sodium bicarbonate solution (20 ml), two 20 ml portions of water, and a saturated aqueous sodium bicarbonate solution (20 ml) in the order given, and dried over anhydrous magnesium sulfate. The solvent was distilled off therefrom to afford the title product (yield 0.2 g, 26%). The NMR spectrum of this product agreed with that of the object product as obtained by method (A).

Production of 15-dehydro prostaglandin B$_1$ methyl ester 7-(2-Bromo-5-oxo-1-cyclopentenyl) heptanoic acid methyl ester (101.3 mg, 0.33 mmole) was mixed with 1-octene-3-one (53.7 mg, 10.43 mmole), and then triethylamine (50.4 mg, 0.50 mmole), palladium diacetate (1.4 mg, 0.006 mmole) and triphenyl phosphine (3.4 mg, 0.013 mmole) were added thereto. The mixture was heated in a sealed tube wherein air had been replaced by argon gas, at 100° C. for 24 hours. The reaction mixture was dissolved in ether (3 ml), and the insoluble matter was removed by filtration. The solvent was distilled off from the filtrate to give a residue. The residue was purified by silica gel column chromatography using as a solvent a mixture of hexane and ethyl acetate, to afford 15-dehydro PGB$_1$ methyl ester (yield 73.7 mg, 63.4%). The NMR, IR, and MS spectra, and TLC of this product agreed with those of a sample produced by a previously known method of synthesis.

PGB$_1$ is an abbreviation for prostaglandin B$_1$.

Example 2

15-dehydroprostaglandin B$_1$ methyl ester 7-(2-Bromo-5-oxo-1-cyclopentenyl) heptanoic acid methyl ester (93.2 mg, 0.31 mmole) as produced above, was mixed with 1-octene-3-one (50.8 mg, 0.40 mmole), and then triethylamine (42.3 mg, 0.42 mmole), palladium diacetate (2.4 mg, 0.01 mmole) and triphenyl phosphine (4.1 mg, 0.016 mmole) were added thereto. The mixture was heated in a sealed tube wherein air had been replaced by argon gas, at 100° C. for 26 hours and 20 minutes. The reaction mixture was dissolved in ether (3 ml), and the insoluble substance was removed by filtration. The solvent was distilled off from the filtrate. The resultant mixture thus obtained was separated by purification by silica gel column chromatography in the same manner as above to obtain 15-dehydro PGB$_1$ methyl ester (yield 78 mg, 72.8%). The NMR spectrum, the IR spectrum, and the TLC of the product agreed with those of a sample produced by a known method of synthesis.

Example 3

15-dehydro prostaglandin B$_1$ methyl ester 7-(2-Bromo-5-oxo-1-cyclopentenyl) heptanoic acid methyl ester (146.3 mg, 0.48 mmole) as produced above, was mixed with 1-octene-3-one (142.7 mg, 1.15 mmole), and then triethylamine(156.4 mg, 1.55 mmole) and a catalyst (a mixture of palladium diacetate and triphenyl phosphine in a ratio of 1:2, 5.6 mg) were added thereto. The mixture was heated in a sealed tube wherein air had been replaced by argon gas, at 100° C. for 24 hours. The reaction mixture was dissolved in ether (3 ml), and the insoluble matter was removed by filtration. The solvent was distilled off from the filtrate. The resultant mixture was separated by silica gel column chromatography using as a solvent a mixture of hexane and ethyl acetate, to recover 7-(2-bromo-5-oxo-1-cyclopentenyl) heptanoic acid methyl ester (yield 9.8 mg, 6.7%) and obtain 15-dehydro PGB$_1$ methyl ester (yield 133 mg, 79.6%). The NMR spectrum, the IR spectrum, and the TLC of the product agreed with those of a sample produced by a known method of synthesis.

Example 4

15-dehydroprostaglandin B$_1$ methyl ester 7-(2-Bromo-5-oxo-1-cyclopentenyl) heptanoic acid methyl acid (80 mg, 0.26 mmole) and 1-octene-3-one (60.6 mg, 0.48 mmole) were dissolved in acetonitrile (10 ml), and then triethylamine (56.2 mg, 0.56 mmole) and a catalyst (a mixture of palladium diacetate and triphenylphosphine in a ratio of 1:2, 2.4 mg) were added thereto. The mixture was refluxed by heating under an argon atmosphere for 46 hours and 30 minutes. The reaction mixture was cooled and then subjected to filtration. The solvent was distilled off and the residue thus obtained was purified by silica gel column chromatography using as a solvent a mixture of hexane and ethyl acetate to recover 7-(2-bromo-5-oxo-1-cyclopentenyl)heptanoic acid methyl ester (yield 72 mg, 90%) and obtain 15-dehydro PGB$_1$ methyl ester (yield 4.5 mg, 5%). The NMR spectrum, the IR spectrum, and the TLC of the product agreed with those of a sample produced by the previously known method of synthesis.

Example 5

15-dehydro prostaglandin B$_1$ methyl ester 7-(2-Bromo-5-oxo-1-cyclopentenyl) heptanoic acid methyl ester (78 mg, 0.26 mmole) as produced above, was mixed with 1-octene-3-one (53.4 mg, 0.42 mmole), and then triethylamine (646.7 mg, 6.4 mmole), acetic acid (145.6 mg, 2.4 mmole), and a catalyst (a mixture of palladium diacetate and triphenyl phosphine in a ratio of 1:2, 9.2 mg) were added thereto. The mixture was heated in a sealed tube wherein air had been replaced by argon gas, 100° C. for 24 hours. The reaction mixture was dissolved in ether (10 ml), washed with three 10 ml portions of water and then two 10 ml portions of a saturated aqueous sodium chloride solution, and dried over anhydrous magnesium sulfate. The solvent was distilled off therefrom. The resultant mixture was separated by silica gel column chromatography, to recover 7-(2-bromo-5-oxo-1-cyclopentenyl) heptanoic acid methyl ester (yield 13.3 mg, 17%), and obtain 15-dehydro $PGB_1$ methyl ester (yield 24.4 mg, 27.3%) and 13,14-dihydro-15-dehydro $PGB_1$ methyl ester (yield 21.0 mg, 23.3%). The NMR spectrum, the IR spectrum, and the TLC of the product, agreed with those of a sample produced by a previously known method of synthesis.

Example 6

15-dehydro prostaglandin $B_1$ methyl ester 7-(2-Bromo-5-oxo-1-cyclopentenyl) heptanoic acid methyl ester (98.8 mg) as produced above, was dissolved in dried acetone (5 ml), and a dried sodium iodide (0.5 g) and para-toluene sulfonic acid (0.05 g) were added thereto at room temperature. The mixture thus obtained was stirred for 21 hours and subjected to filtration. The precipitate was washed well with ether, and the ether thus washed was combined with the filtrate as obtained above, and then concentrated to a solid substance. Ether (20 ml) was added to the substance and the solution thus obtained was washed with water (20 ml) and a saturated aqueous sodium chloride solution (20 ml), and dried over anhydrous magnesium sulfate. The solvent was distilled off therefrom to afford 7-(2-iodo-5-oxo-1-cyclopentenyl) heptanoic acid methyl ester (yield 110 mg, 96%0.

IR Spectrum (Liquid film) $cm^{-1}$: 1730, 1695, 1605.

7-(2-Iodo-5-oxo-1-cyclopentenyl) heptanoic acid methyl ester (79.5 mg, 0.23 mmole) was mixed with 1-octene-3-one (62.5 mg 0.5 mmole), and triethyl amine (51.3 mg, 0.51 mmole) and a catalyst (a mixture of palladium diacetate and triphenyl phosphine in a ratio of 1:2, 6.7 mg) were added thereto. The mixture was heated at 100° C. for 24 hours in a sealed tube wherein the air had been replaced by argon gas. The reaction mixture was dissolved in ether (3 ml) and then filtered. The solvent was distilled off from the filtrate, and the resultant residue was purified by silica gel column chromatography using as a solvent a mixture of hexane and ethyl acetate to obtain 15-dehydro $PGB_1$ methyl ester (yield 43.3 mg, 54%). The NMR spectrum, the IR spectrum, and the TLC of this product agreed with those of a sample produced by a previously known method of synthesis.

Example 7

Prostaglandin $B_1$ methyl ester (9-oxo-15-hydroxy prosta-8,13-dienoic acid methyl ester)

7-(2-Bromo-5-oxo-1-cyclopentenyl) heptanoic acid methyl ester (83.3 mg, 0.28 mmole) was mixed with 1-octene-3-ol (47.3 mg, 0.37 mmole), and then triethyl amine (42.1 mg, 0.42 mmole), palladium diacetate (1.4 mg, 0.006 mmole), and triphenyl phosphine (3.6 mg, 0.013 mmole) were added thereto. The mixture thus obtained was heated at 100° C. for 21 hours and 45 minutes in a sealed tube wherein air had been replaced by argon gas. The reaction mixture was dissolved in ether (3 ml) and filtered. The filtrate was concentrated.

The mixture thus obtained was separated by silica gel column chromatography using as a solvent a mixture of hexane and ethyl acetate to obtain $PGB_1$ methyl ester (yield 40.1 mg, 41.7%), 13,14-dihydro-15-dehydro $PGB_1$ methyl ester (yield 23 mg, 24%), 15-dehydro $PGB_1$ methyl ester (yield 10.3 mg, 10.8%), and 7-(2-bromo-5-oxo-1-cyclopentenyl) heptanoic acid methyl ester (yield 12.0 mg, 14.4%). The NMR spectrum, the IR spectrum, and the TLC of each product agreed with those of a sample produced by a previously known method of synthesis.

Example 8

Prostaglandin $B_1$ (9-oxo-15-hydroxy prosta-8,13-dienoic acid)

A dried triphenyl phosphine (288 mg) was dissolved in a dried benzene (10 ml), and then 1M bromine in benzene solution (1.1 ml) was added thereto while stirring at 0° C. over 3 minutes. The mixture was stirred for 10 minutes at room temperature, and then dried triethyl amine (0.15 ml) was added thereto at 0° C. Continuously, 7-(2,5-dioxocyclopentyl) heptanoic acid (113 mg) were added thereto. The mixture was stirred for 26 hours, and poured into the same volume of water. The aqueous solution was extracted with three 20 ml portions of ether. The ether layer was washed with water and saturated aqueous sodium chloride solution, and then dried over anhydrous magnesium sulfate. The reaction mixture was purified by thin layer chromatography to afford 7-(2-bromo-5-oxo-1-cyclopentenyl) heptanoic acid (yield 96.6 mg, 67%).

IR Spectrum (Liquid film) $cm^{-1}$: 1730, 1700, and 1620.

NMR Spectrum ($CDCl_3$, internal standard: TMS).

δ: 1.2–1.8 (m, 8H): methylene group in 3 to 6 positions; 2.1–2.45 (m, 4H), 2.45–2.7 (m, 2H) and 2.8–3.0 (m, 2H): methylene group in 2, 7, 10, and 11 positions.

7-(2-Bromo-5-oxo-1-cyclopentenyl) heptanoic acid (40.9 mg, 0.14 mmole) was mixed with 1-octene-3-ol (61.3 mg, 0.49 mmole), and then triethyl amine (796.7 mg, 7.9 mmole) and a catalyst (a mixture of palladium diacetate and triphenyl phosphine in a ratio of 1:2, 6.6 mg) were added thereto. The mixture was heated at 100° C. for 24 hours in a sealed tube wherein the air had been replaced by argon gas.

The reaction mixture was dissolved in ether (10 ml) and washed with the same volume of 1N aqueous hydrochloric acid solution. The aqueous layer was extracted with the same volume of ether. The ether layer was washed with the same volume of water three times and with saturated aqueous sodium chloride solution two times, and then dried over anhydrous magnesium sulfate. The reaction mixture was concentrated and thereafter purified by thin layer chromatography using as a solvent a mixture of methanol and chloroform, to recover 7-(2-bromo-5-oxo-1-cyclopentenyl) heptanoic acid (yield 12.1 mg, 29.6%) and obtain $PGB_1$ (yield 13.1 mg, 27.5%). The NMR spectrum, the IR spectrum, and the TLC of this product agreed those of a sample produced by a previously known method of synthesis.

Example 9

13,14-dehydro prostaglandin B₁ methyl ester

(9-oxo-15-hydroxy prosta-8-ene-13-ynoic acid methyl ester)

7-(2-Bromo-5-oxo-1-cyclopentenyl) heptanoic acid methyl ester (62.0 mg, 0.20 mmole) was mixed with 1-octyne-3-ol (39.9 mg, 0.32 mmole), and then triethyl amine (26 mg, 0.26 mmole), palladium diacetate (2.0 mg, 0.009 mmole) and triphenyl phosphine (4.6 mg, 0.018 mmole) were added thereto. The mixture thus obtained was heated at 100° C. for 5 hours in a sealed tube wherein air had been replaced by argon gas. The reaction mixture was dissolved in ether (3 ml), and the solution was filtered. The filtrate was concentrated to a solid. The mixture thus obtained was separated by silica gel column chromatography using as a solvent a mixture of hexane and ethyl acetate to recover 7-(2-bromo-5-oxo-1-cyclopentenyl) heptanoic acid methyl ester (yield 3.1 mg, 5%), and obtain 13,14-dehydro PGB₁ methyl ester (yield 23.5 mg, 33%) and 15-dehydro PGB₁ methyl ester (yield 2.5 mg, 5%). The NMR spectrum, the IR spectrum, and the TLC of each product agreed with those of samples produced by previously known methods of synthesis.

Example 10

15-t-butyl dimethylsiloxy prostaglandin B₁ methyl ester

(9-oxo-15-t-butyldimethylsiloxy prosta-8,13-dienoic acid methyl ester)

7-(2-Bromo-5-oxo-1-cyclopentenyl) heptanoic acid methyl ester (119.5 mg, 0.39 mmole) was mixed with 3-t-butyl dimethylsiloxy octene (158.3 mg, 0.65 mmole), and then triethyl amine (72.0 mg, 0.71 mmole), and a catalyst (a mixture of palladium diacetate and triphenyl phosphine in a ratio of 1:2; 8.5 mg) were added thereto. The mixture thus obtained was heated at 100° C. for 24 hours in the sealed tube wherein air had been replaced by argon gas. The reaction mixture was dissolved in ether (3 ml) and the solution was filtered. The filtrate was concentrated to a solid state, and the mixture thus obtained was separated by silica gel column chromatography using as a solvent a mixture of hexane and ethyl acetate to recover 7-(2-bromo-5-oxo-1-cyclopentenyl) heptanoic acid methyl ester (yield 3.9 mg, 1.3%) and obtain t-butyldimethylsilyloxy PGB₁ methyl ester (yield 167.2 mg, 92%). The NMR spectrum, the IR spectrum, and the TLC of this product agreed with those of a sample produced by previously known method of synthesis.

Example 11

13,14-dehydro-15-t-butyldimethylsilyloxyprostaglandin B₁ methyl ester

(9-oxo-15-t-butyldimethylsilyloxy-8-ene-13-ynoic acid methyl ester)

7-(2-Bromo-5-oxo-1-cyclopentenyl) heptanoic acid methyl ester (112.5 mg, 0.37 mmole) was mixed with 3-t-butyldimethylsilyloxy octyne (127.7 mg, 0.53 mmole), and then triethyl amine (159.0 mg, 1.57 mmole), and a catalyst (a mixture of palladium diacetate and triphenylphosphine in a ratio of 1:2, 9.8 mg) were added thereto. The mixture thus obtained was heated at 100° C. for 24 hours in a sealed tube wherein air had been replaced by argon gas. The reaction mixture was dissolved in ether (3 ml), and the solution was filtered.

The filtrate was concentrated to a solid state. The mixture thus obtained was separated by silica gel column chromatography using as a solvent a mixture of hexane and ethyl acetate, to obtain the title compound (yield 89.1 mg, 45%). The NMR spectrum, the IR spectrum, and the TLC of this product agreed with those of a sample produced by a previously known method of synthesis.

We claim:

1. A method for the production of a cyclopentenyl-heptanoic acid derivative of the formula:

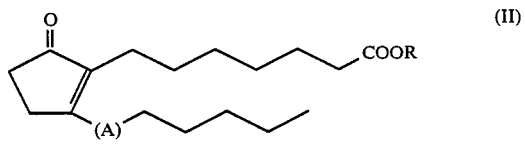

wherein R is a radical selected from the group consisting of hydrogen and alkyl groups having from 1 to 4 carbon atoms, and -(A)- is a member selected from the group consisting of:

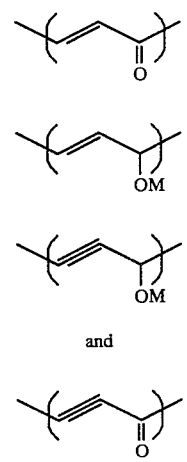

and wherein M is hydrogen or triorganosilyl, which comprises:

(1) reacting a cyclooctene derivative of the formula:

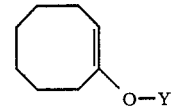

wherein Y is a member selected from the group consisting o —R¹, —COR¹ and —SiR²₃, wherein R¹ is alkyl, aryl or aralkyl, and R² is $C_{1-5}$ alkyl, with a compound of the formula:

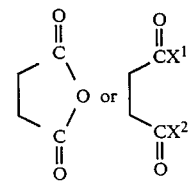

wherein each of $X^1$ and $X^2$ is halogen, thereby obtaining a heptanoic acid derivative having the formula:

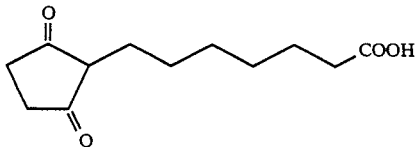

(2) reacting the heptanoic acid derivative of the formula (III) with a halogen and a triorganophosphorus compound, and, if desired, converting the resulting product to the $C_1$ to $C_4$ alkyl ester derivative thereof, thereby obtaining a compound of the formula:

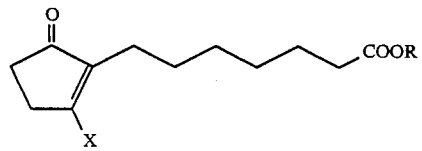

wherein R is as previously defined and X is a halogen atom; and (3) reacting the compound of formula (I) with a compound selected from the group consisting of:

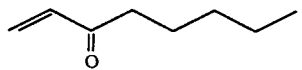

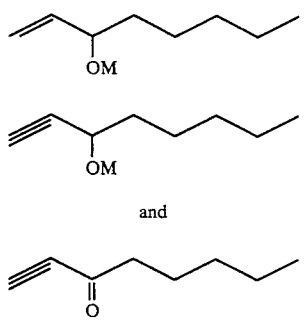

and wherein M is as previously defined in the presence of a palladium salt and an organophosphorus compound or an amine or a combination of an organophosphorus compound and an amine.

2. The method of claim 1, wherein said palladium salt is palladium acetate, said organophosphorus compound is triphenylphosphine and saids amine is triethylamine.

3. The method of claim 1, wherein, in step (3), said reaction is conducted in a solvent selected from the group consisting of acetonitrile, N,N'-dimethylformamide and an alcohol.

4. The method of claim 1, wherein, in step (2), said halogen reactant is chlorine, bromine or iodine and said triorganophosphorus compound is triphenylphosphine.

5. The method of claim 4, wherein the halogenation reaction of step (2) is achieved with the combination of bromine and triphenylphosphine.

6. The method of claim 1, wherein the halogenation reaction of step (2) is conducted in a solvent of benzene, toluene, DMF, benzonitrile or acetonitrile.

7. The method of claim 1, wherein, in step (3), said reaction in conducted without the presence of a solvent.

* * * * *